United States Patent [19]
Van Der Meyden et al.

[11] Patent Number: 6,132,401
[45] Date of Patent: Oct. 17, 2000

[54] SAFETY SYRINGE

[75] Inventors: Hendrikus J Van Der Meyden, Midrand; Alexis A Wadman, Bedfordview, both of South Africa

[73] Assignee: Nordway Limited, United Kingdom

[21] Appl. No.: 09/180,228

[22] PCT Filed: May 6, 1997

[86] PCT No.: PCT/GB97/01232

§ 371 Date: Nov. 4, 1998

§ 102(e) Date: Nov. 4, 1998

[87] PCT Pub. No.: WO97/41908

PCT Pub. Date: Nov. 13, 1997

[30] Foreign Application Priority Data

May 3, 1996 [ZA] South Africa ............................ 96/3499

[51] Int. Cl.[7] .............................. A61M 5/32; A61M 5/00
[52] U.S. Cl. ........................ 604/195; 604/110; 604/198
[58] Field of Search ................................. 604/110, 188, 604/195, 198, 214, 218, 231, 240, 242, 243, 264, 272, 203

[56] References Cited

U.S. PATENT DOCUMENTS 5,320,606  6/1994  Jore .
5,656,031  8/1997  Thorne et al. ........................... 604/110

FOREIGN PATENT DOCUMENTS 0 581 523 A1  2/1994  European Pat. Off. .
41 20 267 A1  12/1992  Germany .
728248  4/1955  United Kingdom .

Primary Examiner—Glenn K. Dawson
Assistant Examiner—Michael J Hayes
Attorney, Agent, or Firm—Knobbe Martens Olson & Bear, LLP

[57] ABSTRACT

The invention concerns a safety syringe in which the needle may be held within a sheath both before and particulary after use without handling. The syringe consists essentially of a generally tubular protective sheath carrying piston engaging formations and having a needle end and an opposite rear end; a piston including an elongate piston body and a piston head, there being a fluid pathway through the head and longitudinally through the body, the piston body being operatively locatable to extend within the sheath and be engaged by the piston engaging formations, with the piston head outside the sheath and connected to and in fluid communication with the piston body; a barrel which is slidable in a discharge stroke in use over the outside of the operatively located piston head and along the sheath to a discharged position, to thereby release the piston engaging formations and grip the released piston, the barrel being oppositely slidable from the discharged position to withdraw the released piston substantially from the sheath to a safe locked position relative to the sheath, characterised in that the barrel is shaped and dimensioned to be slidable over the outside of the protective sheath and the piston body and sheath carry clips and stops to operatively lock the piston body relative to the sheath to hold a needle used with the syringe inside the sheath before and after use.

15 Claims, 16 Drawing Sheets

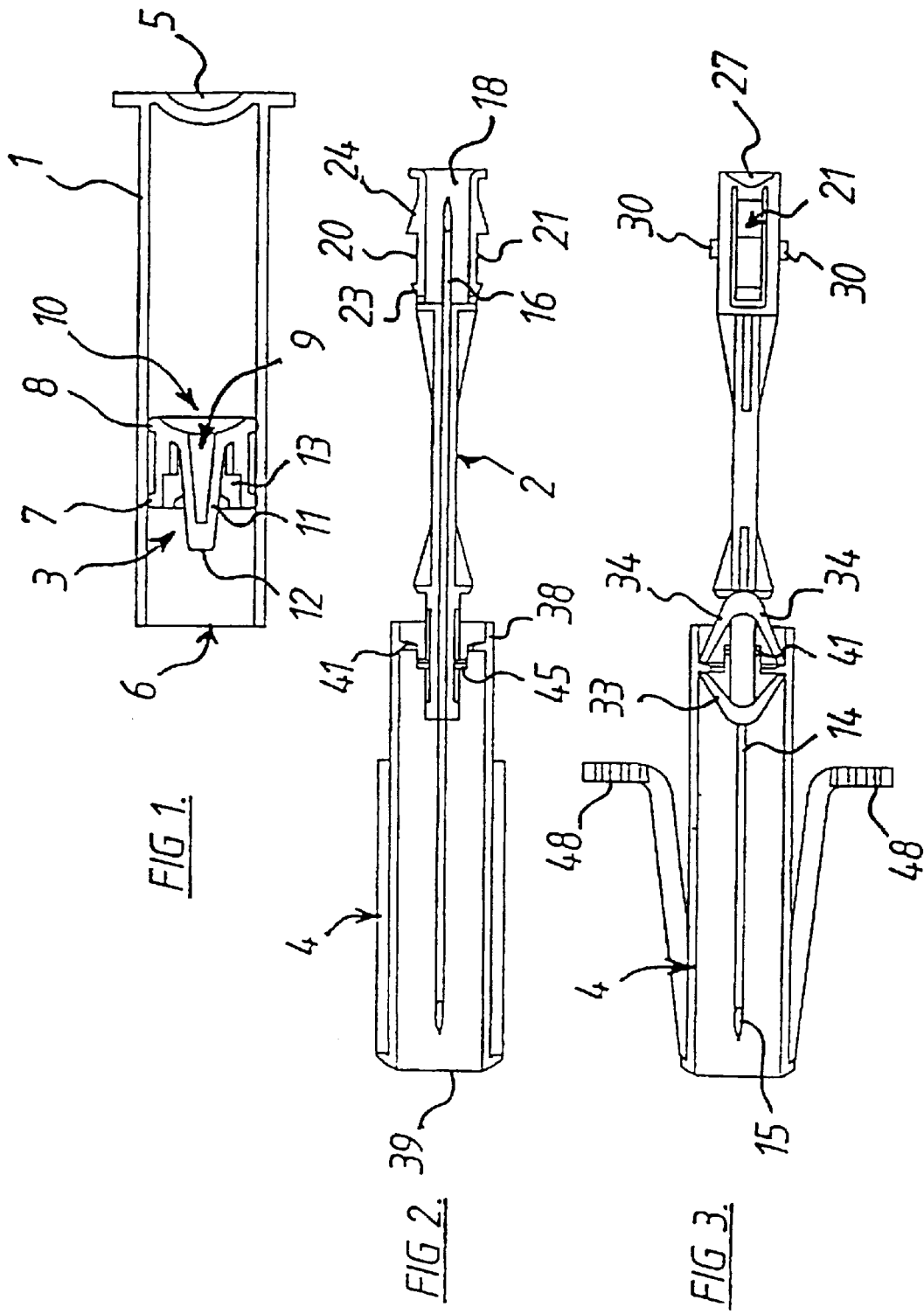

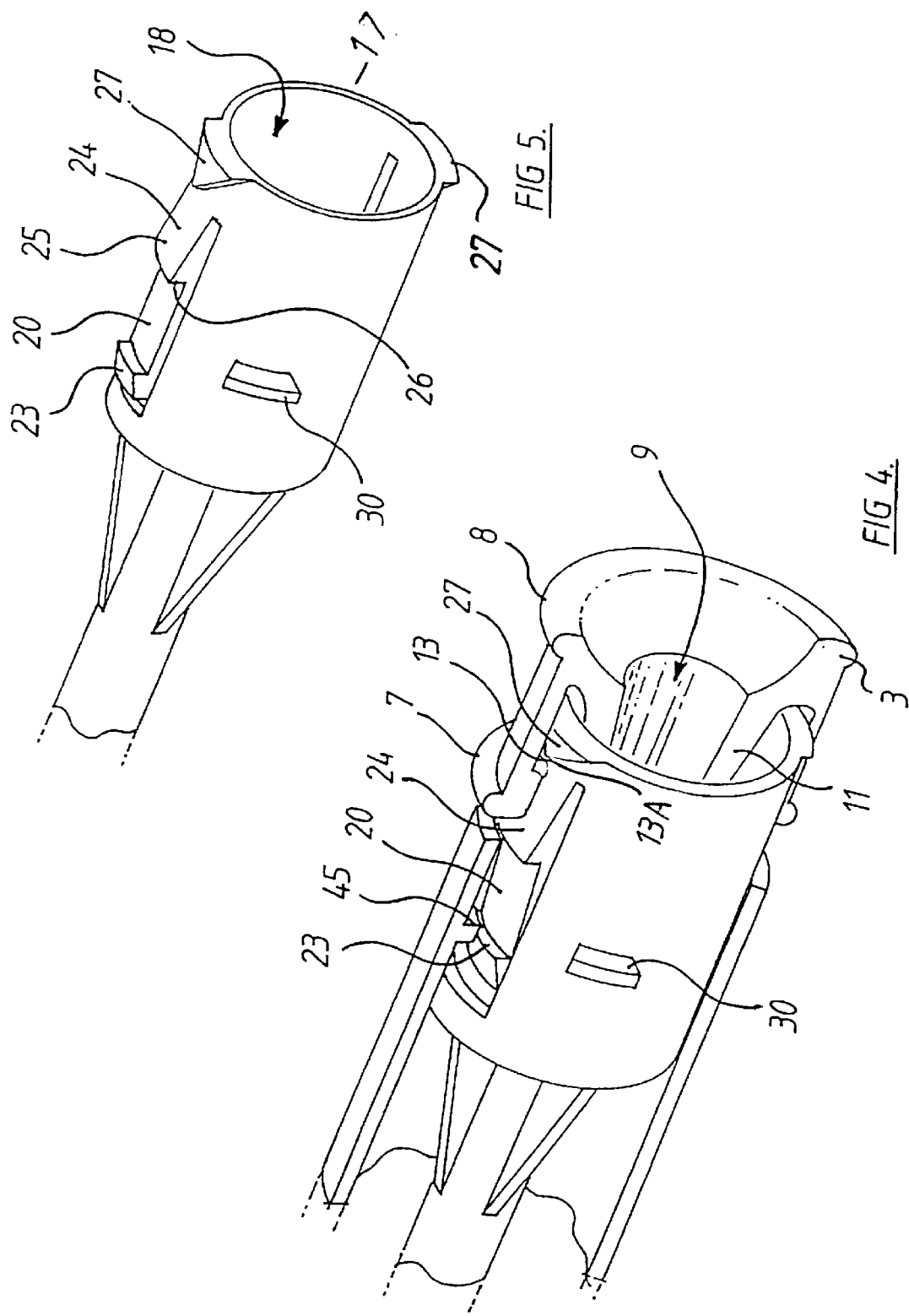

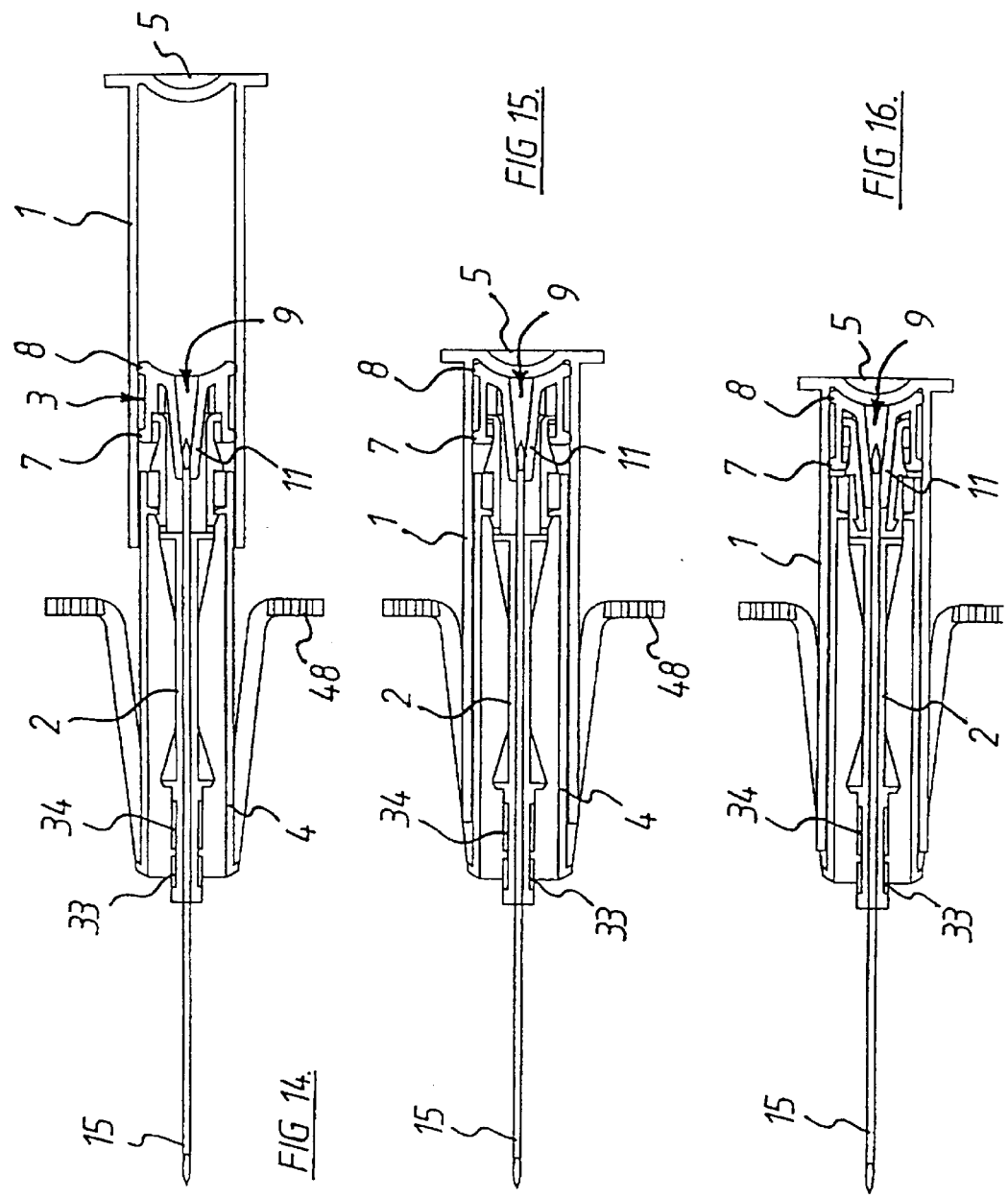

SAFETY SYRINGE

FIELD OF THE INVENTION

This invention relates to a safety syringe.

BACKGROUND TO THE INVENTION

With the increasing risk of infection through needle injuries, there is a demand for a syringe which can be used and disposed of in a manner which reduces the risk of such injury.

OBJECT OF THE INVENTION

It is an object of this invention to provide a safety syringe.

SUMMARY OF THE INVENTION

In accordance with this invention there is provided a syringe comprising: a generally tubular protective sheath carrying piston engaging formations and having a needle end and an opposite rear end;
a piston including an elongate piston body and a piston head, there being a fluid pathway through the head and longitudinally through the body, the piston body being operatively locatable to extend within the sheath and be engaged by the piston engaging formations, with the piston head outside the sheath and connected to and in fluid communication with the piston body;
a barrel which is slidable in a discharge stroke in use over the outside of the operatively located piston head and along the sheath to a discharged position, to thereby release the piston engaging formations, and grip the released piston, the barrel being oppositely slidable from the discharged position to withdraw the released piston substantially from the sheath to a safe locked position relative to the sheath, characterized in that the barrel is shaped and dimensioned to be slidable over the outside of the protective sheath and the piston body and sheath carry clips and stops to operatively lock the piston body relative to the sheath to hold a needle used with the syringe inside the sheath before and after use.

Preferably in a first embodiment of the invention the piston body has a front and a rear end, with front and rear clips thereon, and the sheath has stops at its rear end, the piston body clips and stops being arranged to enable the piston body to be inserted into the sheath with the rear piston body clips engaging the sheath stops and locking the piston body against withdrawal from and insertion into the sheath, in that rotational orientation with the sheath, and being further arranged to enable movement of the barrel to its discharged position to release the rear piston body clips, and to enable the front piston body clips to engage the stops on movement of the piston body to the safe locked position.

There is provided for the sheath to have a first and second axial keyway means, the first keyway means having a cross sectional shape designed to guide a clip rotating therein in use into the second keyway means, and the second keyway means having abrupt edges designed to prevent rotational movement of a clip therein in use.

Further, each of the first and second keyway means are a pair of diametrically opposed matching keyways, with the pairs located at 90 degrees to each other in cross-sectional orientation of the sheath.

Each keyway of a pair has a transverse clip stop, the clip stop of the first keyway pair being located further into the sheath interior than the clip stop of the second keyway pair.

Preferably, the front piston body clips of the piston body form keyway slides, and have opposed clipping formations, being a front formation which is able to slide over the stops in a forward direction only, and a rear formation which is able to slide over the stops in a withdrawal direction only.

The rear piston body clips of the piston body may have opposed clipping formations, being a forward clipping formation slidable over stops on insertion into the sheath, and a rear formation which abuts the stops when the piston body is slid into the sheath.

Preferably, the rear formation of the rear piston body clips is shaped to co-operate with the piston head, on movement of the piston head with the barrel at the end of a discharge stroke in use, to disengage the forward formation of the rear piston body clip from its stop in use.

Alternatively, the piston engaging formations on the sheath may include barbed flaps arranged to engage slots on the piston.

Preferably, these flaps are part of the sheath wall and project axially rearwardly from a hinged portion of the sheath at the needle end of the sheath, the sheath having free ends engagable by the end of the barrel at the end of a discharge stroke to hinge the flaps outwardly and out of engagement with the slots.

Further, the slots are carried in diametrically opposed piston clips which extend axially from the piston body at a front end thereof, and are resiliently inwardly deformable.

The sheath may have the same keyway configuration. To this end the sheath may have a first and second axial keyway means, the first keyway means having a cross sectional shape designed to guide a clip rotating therein in use into the second keyway means, and the second keyway means having abrupt edges designed to prevent rotational movement of a clip therein in use, each keyway means having a transverse stop at the rear end of the sheath, and in which the clips form keyway slides, arranged to enable insertion of the piston body into the first keyway means with the clip slots engaged in the first keyway means stop, and to enable rotation of the piston body in this location to guide the clips into the second keyway means, free of the second keyway means stop in an insertion direction of the piston body into the sheath, and further to enable the withdrawal of the piston body with the clips in the second keyway means to a position where the clip slots engage the stop at the second keyway means to lock the piston body against insertion and withdrawal.

There is also provided for the piston head to be integral with the piston body.

A further feature of the invention provides for the piston to be separate from the piston body and to be connectable to the piston body to form the piston. In one embodiment the protective sheath and piston body are operatively locatable to extend within the sheath and be engaged by the piston engaging formations, with the piston head outside the sheath and connected to and in fluid communication with the piston body; a barrel which is slidable in a discharge stroke in use over the outside of the operatively located piston head and along the sheath to a discharged position, to thereby release the piston engaging formations and grip the released piston, the barrel being oppositely slidable from the discharged position to withdraw the released piston substantially from the sheath to a safe locked position relative to the sheath, characterized in that the barrel is shaped and dimensioned to be slidable over the outside of the protective sheath and the piston body and sheath carry clips and stops to operatively lock the piston body relative to the sheath to hold a needle used with the syringe inside the sheath before and after use.

BRIEF DESCRIPTION OF THE DRAWING

Embodiments of the invention are described below by way of example only, and with reference to the accompanying drawings, in which:

FIG. 1 is a sectioned longitudinal side view of a barrel and piston head according to the invention;

FIG. 2 is a sectioned longitudinal side view of a piston body and a sheath according to the invention;

FIG. 3 is a sectioned longitudinal side view as for FIG. 2, but rotated through 90 degrees around the sheath and piston body axis;

FIG. 4 is a partially cut away isometric view of the piston head connected to the piston body, and inserted in the sheath;

FIG. 5 is an isometric view of the rear end of the piston body;

FIG. 14 is a view of the assembled syringe with barrel and piston head connected to the sheath and piston body in a loaded condition;

FIG. 15 is a side view of the syringe shown in FIG. 14 after a discharge stroke;

FIG. 16 is a longitudinal side view of the syringe with the barrel in a fully depressed unlocked position;

DETAILED DESCRIPTION OF THE DRAWINGS WITH REFERENCE TO THE DRAWINGS

Figure 6:
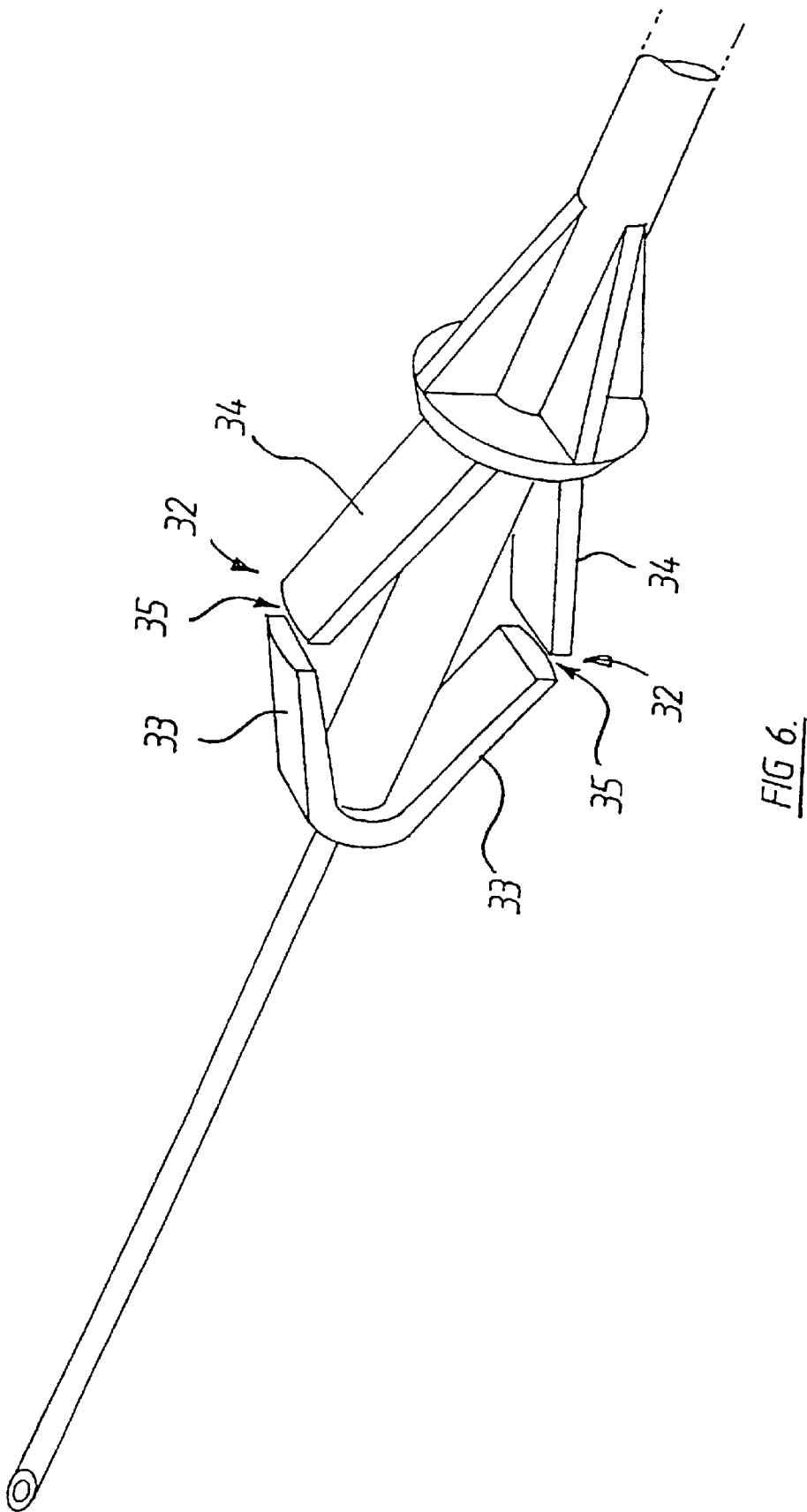
FIG. 6 is an isometric view of the front end of the piston body.
Figure 7:
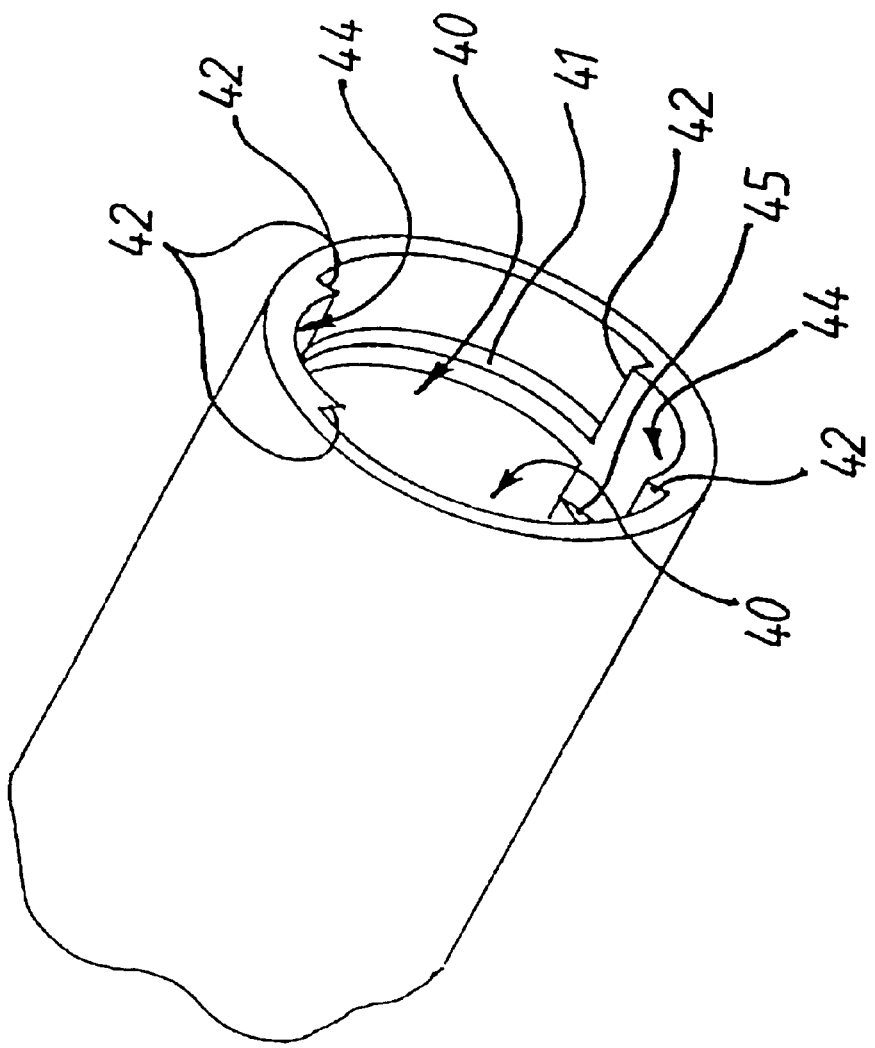
FIG. 7 is an isometric view of the rear entrance to the sheath.
Figure 8:
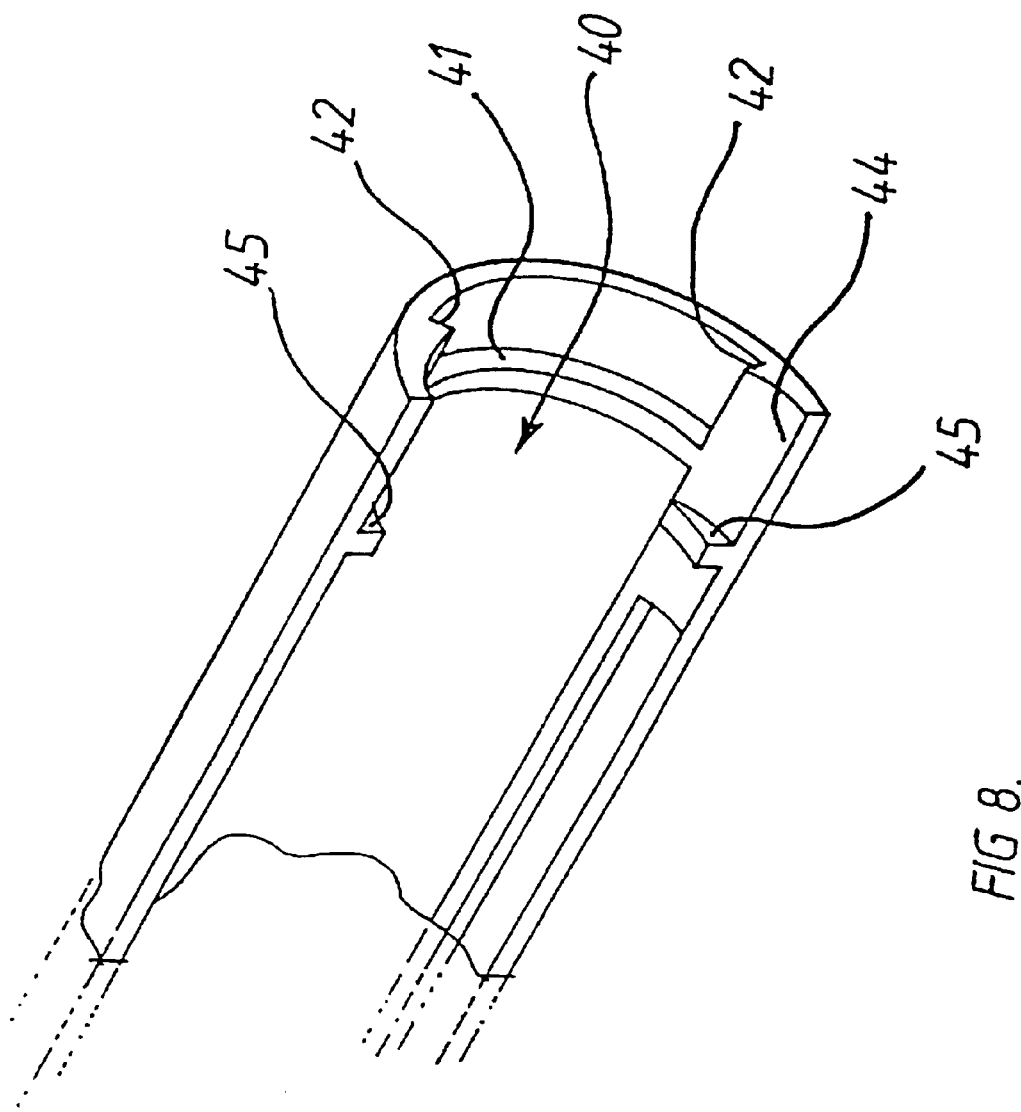
FIG. 8 is an isometric view of the rear end of the sheath cut away for explanatory purposes.
Figure 9:
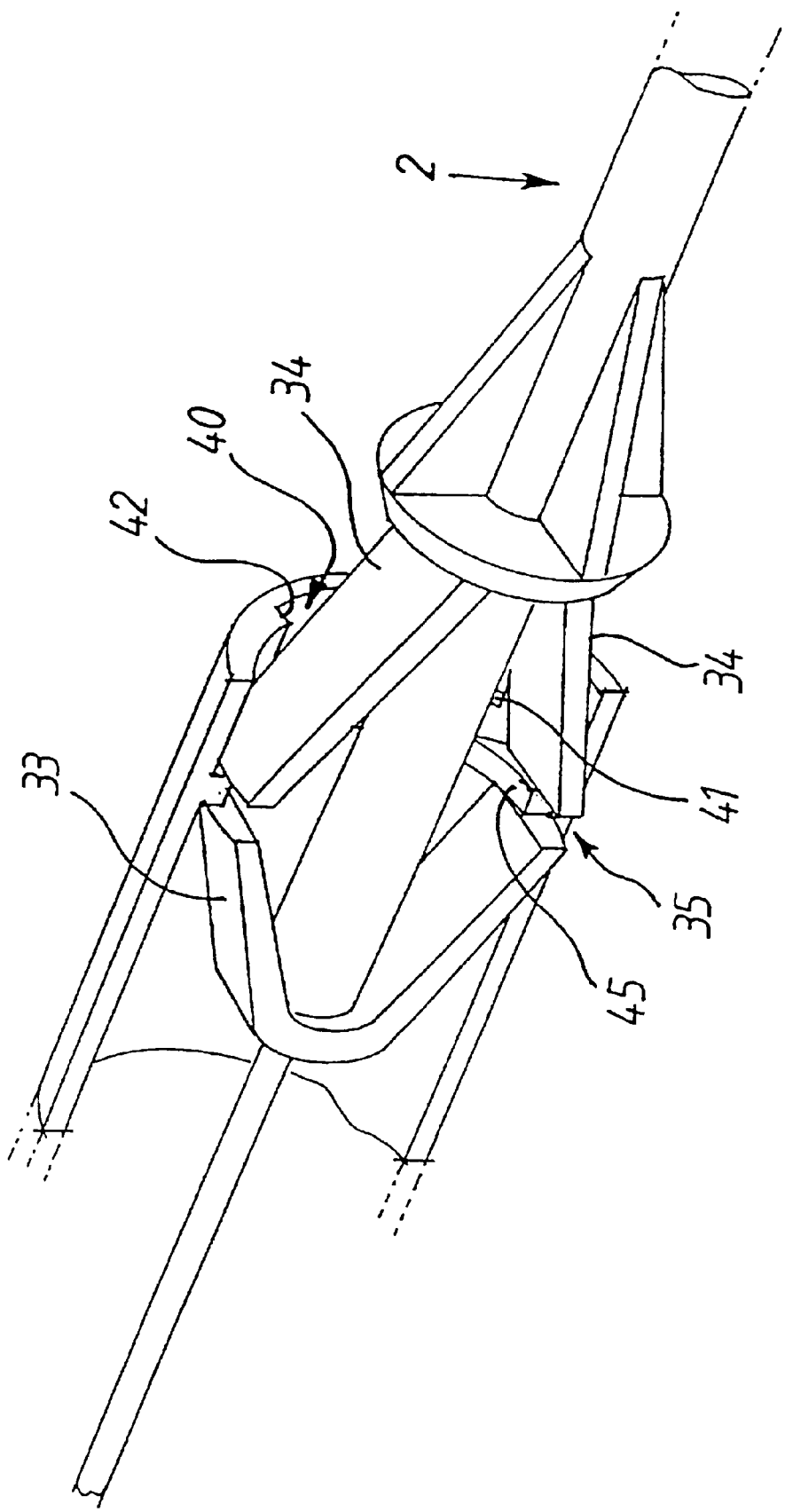
FIG. 9 is a view of the front of the piston body inserted in the sheath in a packaged position.

Referring to FIGS. 1 to 3, a drug delivery system is in the form of a syringe a having a barrel (1), a piston with an elongate piston body (2), and a piston head (3), and a sheath (4).

The barrel is tubular with a closed rear end (5) and an open front or needle end (6), and is preferably made of glass. A stopper may alternatively be provided to close the rear end, enabling the use of a simple length of glass tube for the barrel.

Referring to FIGS. 1 and 4, the piston head (3) is of elastomeric material and is reciprocable within the barrel. It has integral front and rear sealing rings (7) and (8) therearound at each axial end, and a blind axial passageway (9) extending into a rear axial end (10) within a conical projection (11). The projection extends past the front sealing ring (7) where the projection end (12) forms an integral plug to the blind end of the passageway.

The front sealing ring carries an annular radially inwardly extending lip (13) so that opposed recesses (13a) are provided to allow a twist-clip action when the piston is operatively located.

Figure 10:
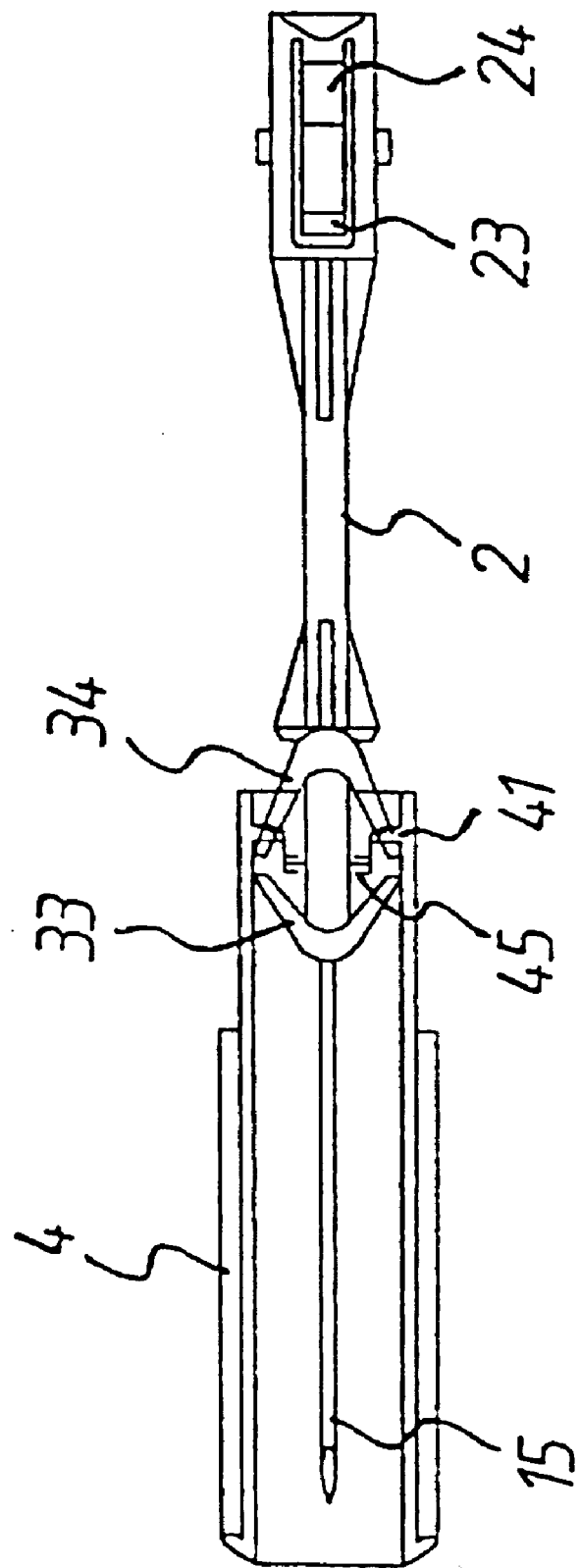
FIG. 10 is a sectioned longitudinal side view of the piston body and sheath after a relative one quarter turn of the piston body within the sheath from the packaged position.

The piston body (2) (FIGS. 2, 3 and 10) has a central hypodermic needle (14) running in its length. The needle (14) extends from a front or needle end (15) to end (16) located just short of, and within, an opposite rear end (7) of the piston body (2).

The rear end (17) of the piston body is shown in more detail in FIGS. 4 and 5. It is tubular, open at the rear, and surrounds the needle rear end (16) (not shown in FIGS. 4 and 5) as it extends into the interior of the tubular space (18).

On diametrically opposed sides of the tubular rear end are hinged rear piston body clips (20) and (21) (not shown in FIGS. 4 and 5). The clips lie within the tubular wall, and extend axially from hinges at their rear ends, to be resiliently pivotable into and out of the tubular space (18). Each clip has two spaced apart outwardly protecting ramp catches, with one catch (23) at its free end and one ramp (24) at its hinged end. The slopes (25) of the ramp catches face away from each other, and the ledges (26) oppose each other.

Positioned at 90 degrees to the clips (20) and (21), on the outside of the rear end of the piston body, are diametrically opposed lateral stops (30).

On the outside of the rear edge are diametrically opposed lugs (27) arranged to co-operate with recesses (13a) of the piston head.

The front end of the piston body is shown in more detail in FIG. 6. Diametrically opposed pairs of barbed clipping formations (32) extend outwardly from the piston body. Each pair (32) has one front piston body clip (33) extending from the body acutely and axially towards the rear of the piston body, and one front piston body clip (34) similarly extending towards the front of the body in the same plane as its mate, in the form of opposed barbs. The ends of the clips of a pair stop short of each other with a gap (35) between them.

Referring to FIGS. 2, 3, 7 and 8, the sheath (4) is shown. It has a rear end (38) and a front or needle end (39). The entrance to the rear end, (FIGS. 7 and 8) is divided into four quarters by two pairs or matching axial keyways. Each keyway of one pair (40) is bound at its axial sides by edges which extend inwardly and towards each other in the manner of a dovetail slot. These keyways have transverse stops (41) which run from edge (42) to edge (42) at the height of the edges, just inwardly of the rear end. Apart from these stops, the keyways run the length of the sheath uninterrupted, and are referred to as the "long" keyways.

The other pair of keyways (44), have no abrupt edges. Each keyway extends smoothly in cross-section, from and at the height of, the axial edges (42) to a central depth equal to the depth of the long keyways. The second keyways each have a transverse stop (45) extending arcuately across them at the height of the edges (42). The stops (45) are spaced inwardly of the stops (41) from the rear end of the piston body. The smooth cross-sectional shape of the second pair of keyways provide a cam action in use, and these keyways are referred to as the "cam" keyways.

The sheath has two finger grips (48) set diametrically opposite each other, and extending from the front end (39) of the sheath outwardly.

In use, the syringe is provided in a packaged condition as illustrated in FIGS. 1 to 3. This position is achieved by preloading the barrel (1) with a required fluid, and inserting the piston head (3) therein to act as a stopper. Suitable covering or other sealing may be provided for the purposes of maintaining sterility. The piston body (2) is inserted into the sheath at the entrance end thereof. This is done by aligning the piston body to slide the clips (32) down the cam keyways causing the front clips (33) to clip over the stop (45) and the rear clips (34) to lock behind them. The piston body in this rotational orientation, is locked in position. The needle is fully contained within the sheath and is protected.

To use the syringe, the piston body is rotated one quarter turn (FIG. 10) which causes the both sets of clips (33) and (34) to be radially depressed by the shape of the camming surface of the cam keyways. As the clips align with the long keyways at the end of the quarter turn, they clip resiliently outwardly into them.

Figure 11:
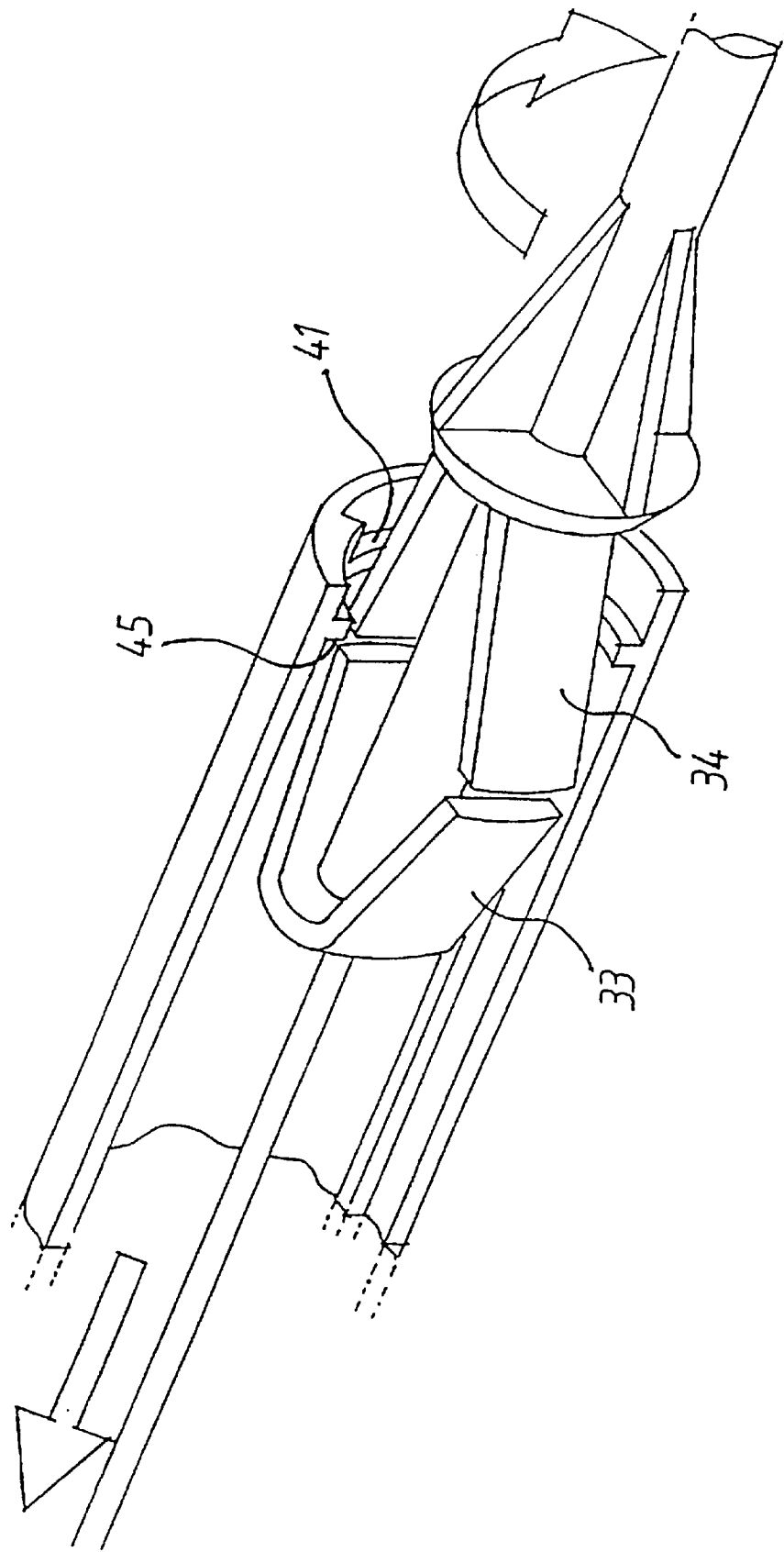
FIG. 11 is an isometric view of the configuration of the embodiment in FIG. 10.

The stops in the keyways are arranged to cause the rear clip (34) to clip outwardly in the keyway past the stop of the long keyway. This position is shown in FIG. 11 in more detail.

Figure 12:
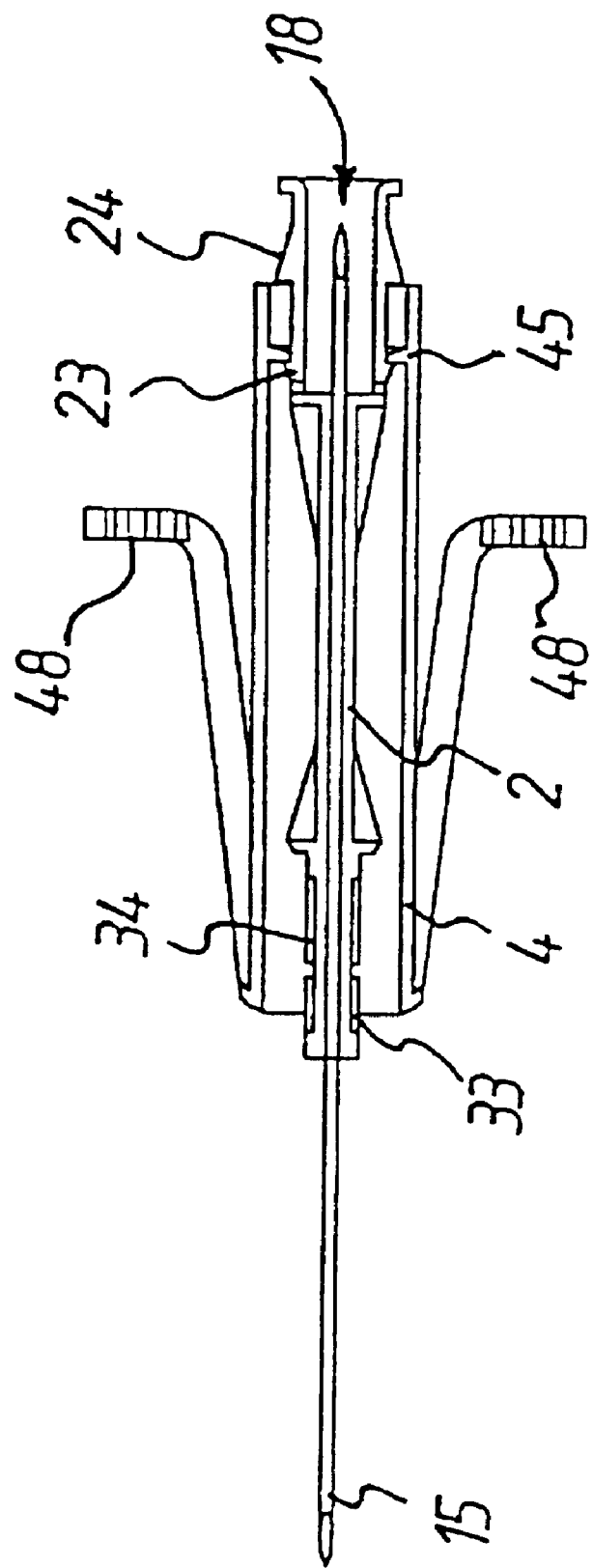
FIG. 12 is a side view of the piston body fully inserted within the sheath in an armed position.
Figure 13:
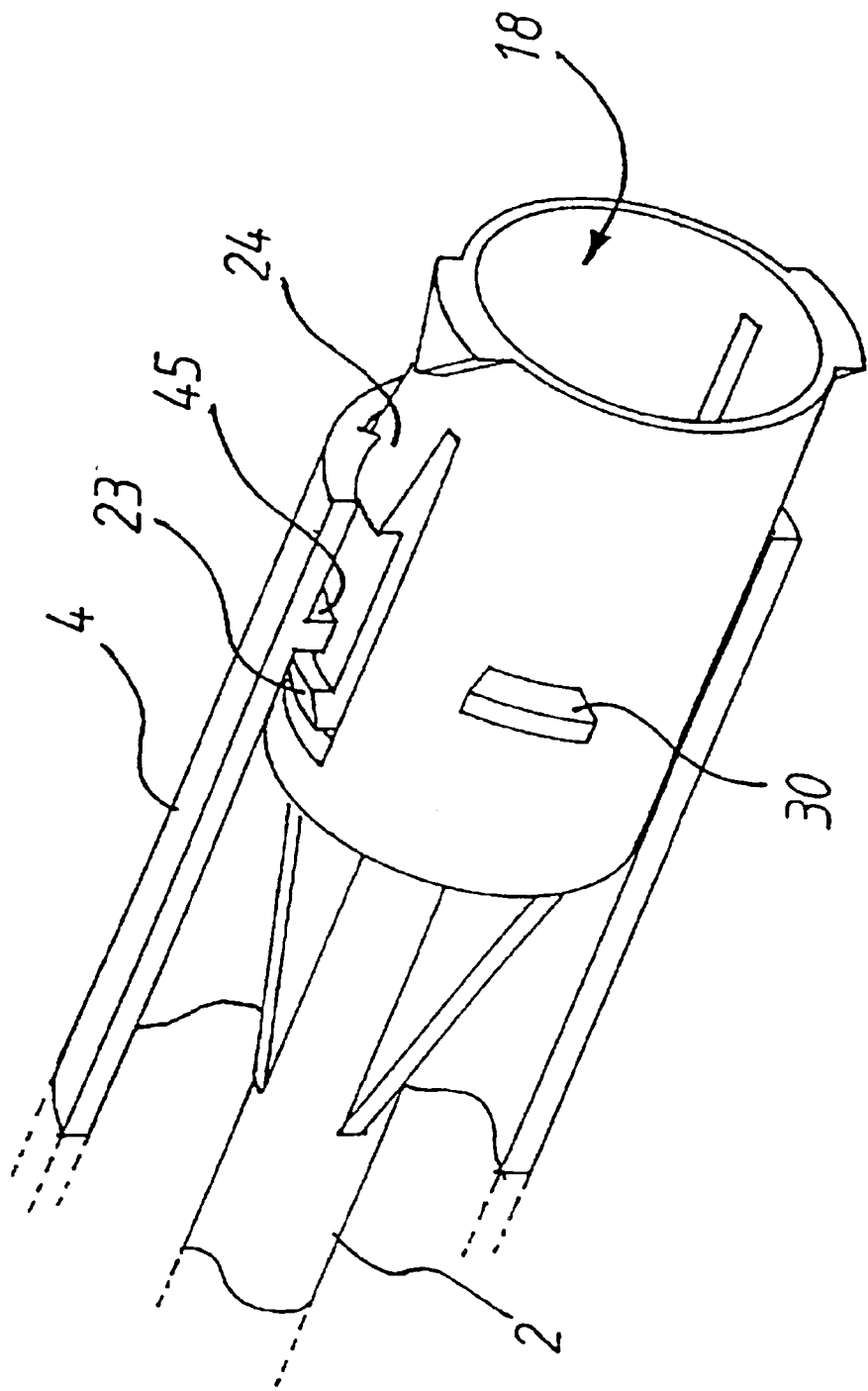
FIG. 13 is a partly sectioned isometric view of the rear of the piston body in the position of FIG. 12.
Figure 17:
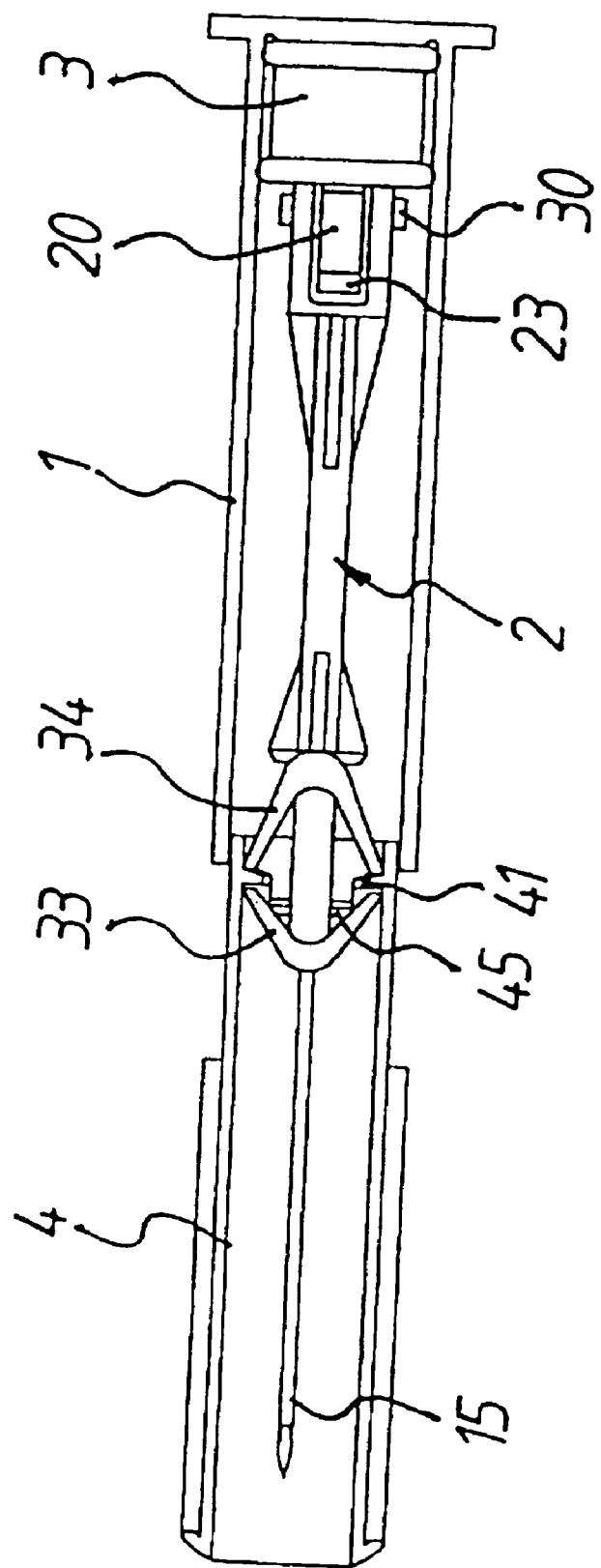
FIG. 17 is a longitudinal side view of the barrel of the syringe with the barrel withdrawn to a safe position.

The piston body may now be slid freely into the sheath with the needle protruding from the front sheath end. As shown in FIG. 12, the piston body is slid until the front catch (23) of the clips (20) at the rear piston body end clip over the transverse stops of the cam keyway (45).

The piston is oriented so that the rear piston clips (20) are at 90 degrees to the front barbed clipping formations (32). In this position, the lateral stops (30) of the rear piston end abut the stops (41) of the long keyway, with the rear ramp catch (24) outside the sheath. The piston body is now locked within the sheath against both further insertion, and withdrawal.

The barrel and piston head, forming a pre-packaged dosage of particular fluid, is now inserted over the piston and the sheath This causes the rear needle end (16) to pierce the end (12) of the projection, and enter the passageway (9), thus causing a complete passageway from the rear end of the piston head, through the needle and the piston body, to the free end of the needle projecting from the sheath. It will be appreciated that at least a piston head portion that reciprocates within the barrel should remain outside the sheath, to avoid the necessity of intermediate seals, and a gripping mechanism to extract the piston, This position is shown in FIG. 14.

Further depression of the barrel over the piston, with the finger supported on the finger grips (48), causes a discharge of the fluid in the piston through the piston head and out of the needle. At the fully depressed position the rear end of the barrel abuts the piston head. (FIG. 15).

To unlock the piston head and piston body, the barrel is further depressed to cause the front flanges of the piston head (3) to slide further over the rear end of the piston body (2). This is shown in FIG. 16, and in detail in FIG. 4. With the piston head contained within the barrel, it cannot expand outwardly away from the clips (20) and the piston head lip (13) rides over the slope of catch (24), thus forcing it to hinge inwardly, and displace the catch (23) from its engaged position over the stop (45).

The barrel is now withdrawn from the sheath, taking the piston head and piston with it under force of friction. The barbed clips (33) and (34) slide in the long keyway until they engage at the top in the entrance to the rear end of the sheath.

Figure 18:
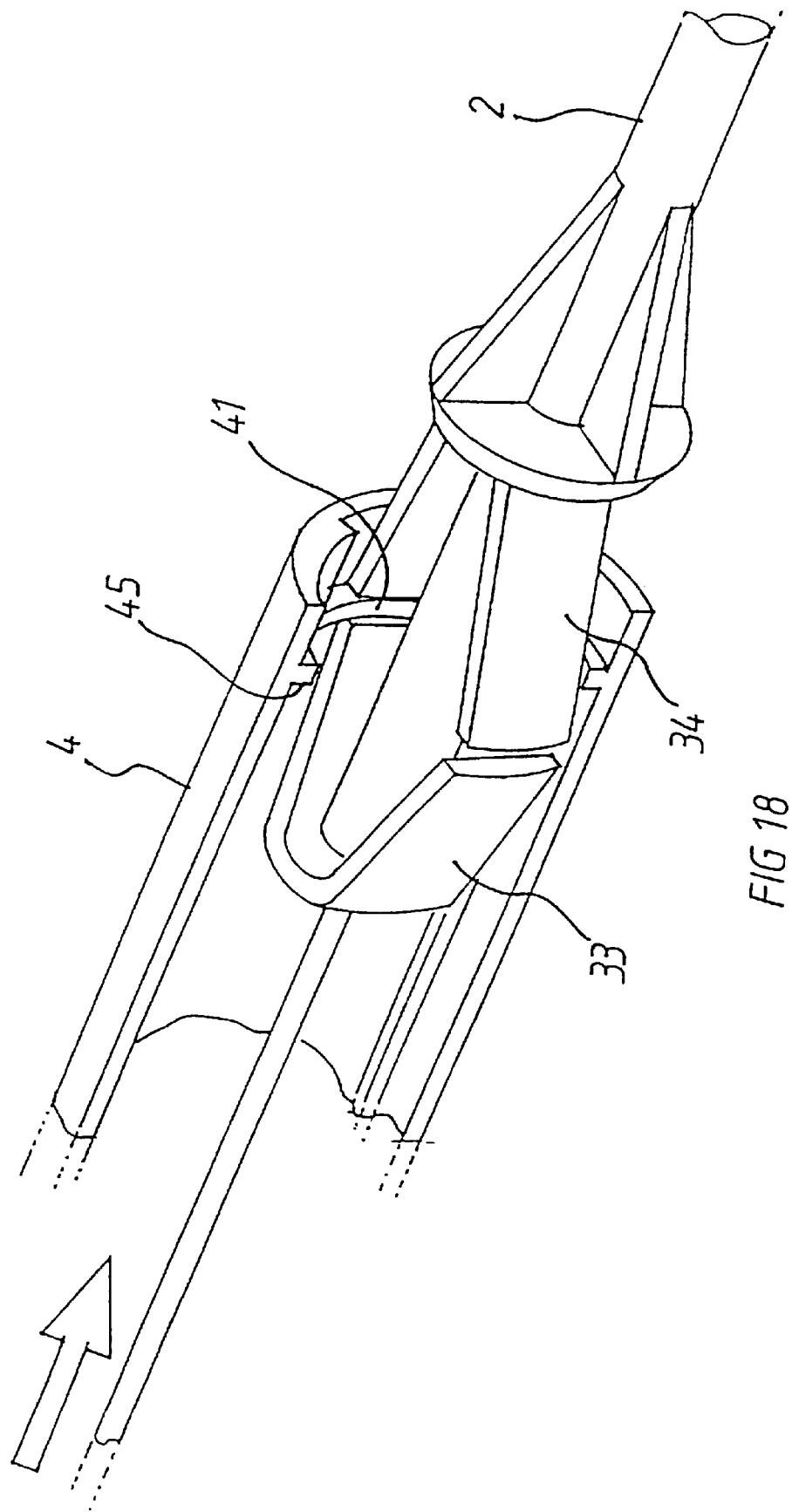
FIG. 18 is a part sectioned isometric view of the front of the piston body clipped into the rear of the sheath with the syringe in the safe position, as shown in FIG. 17.
Figure 19:
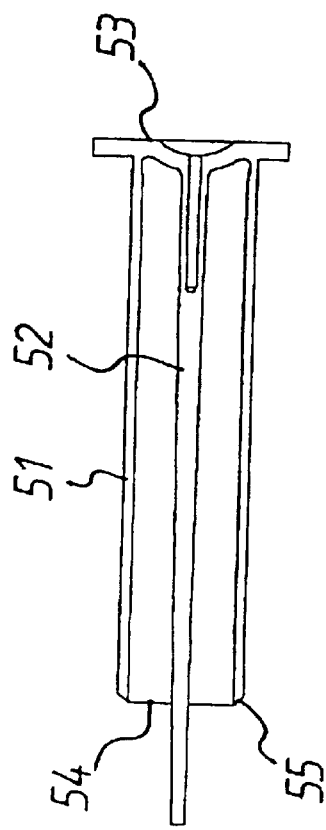
FIG. 19 is a longitudinal side view and cross-section of a barrel of an alternative embodiment of the invention.
Figure 20:
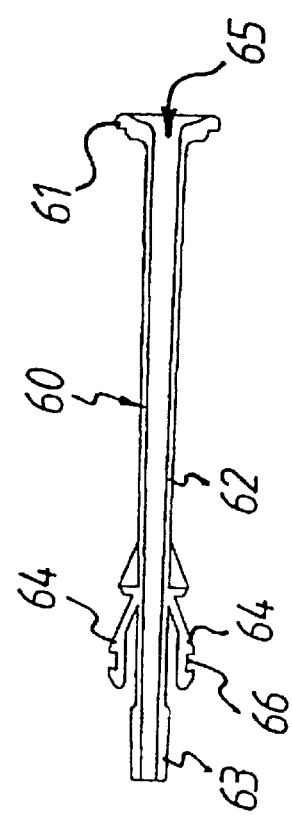
FIG. 20 is a longitudinal cross-section of a piston body and integral piston head of the alternative embodiment.
Figure 21:
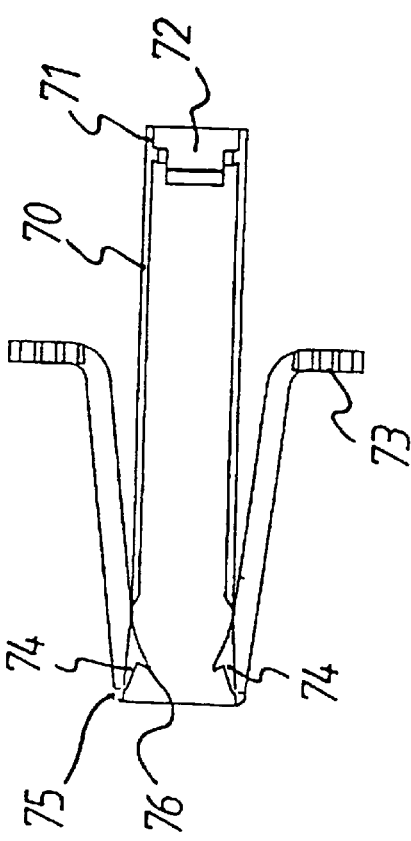
FIG. 21 is a sectioned longitudinal view of a sheath of the alternative embodiment.
Figure 22:
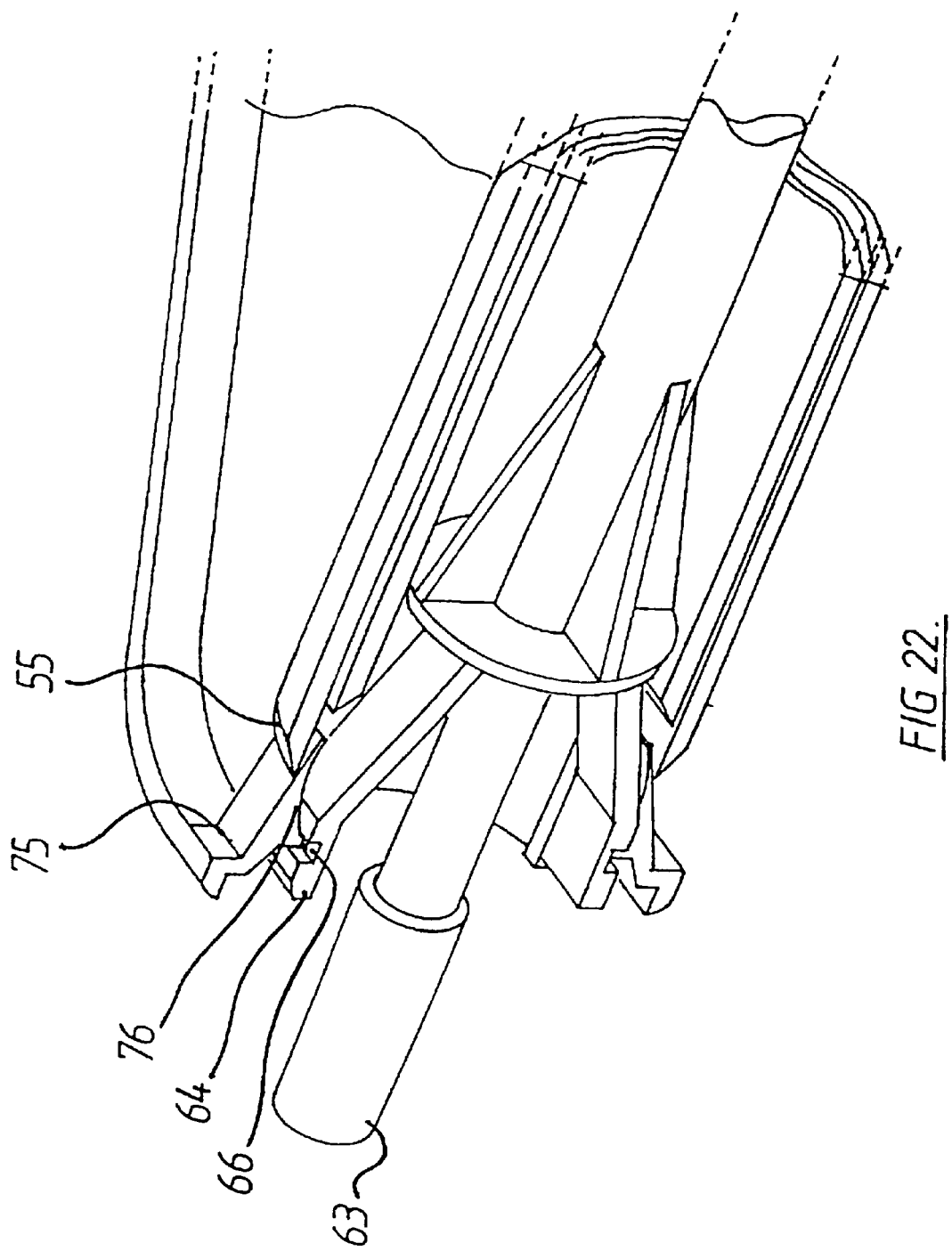
FIG. 22 is a partly sectioned isometric view of the inter-action between the front end of a piston body, the sheath and a piston barrel in the alternative embodiment.
Figure 23:
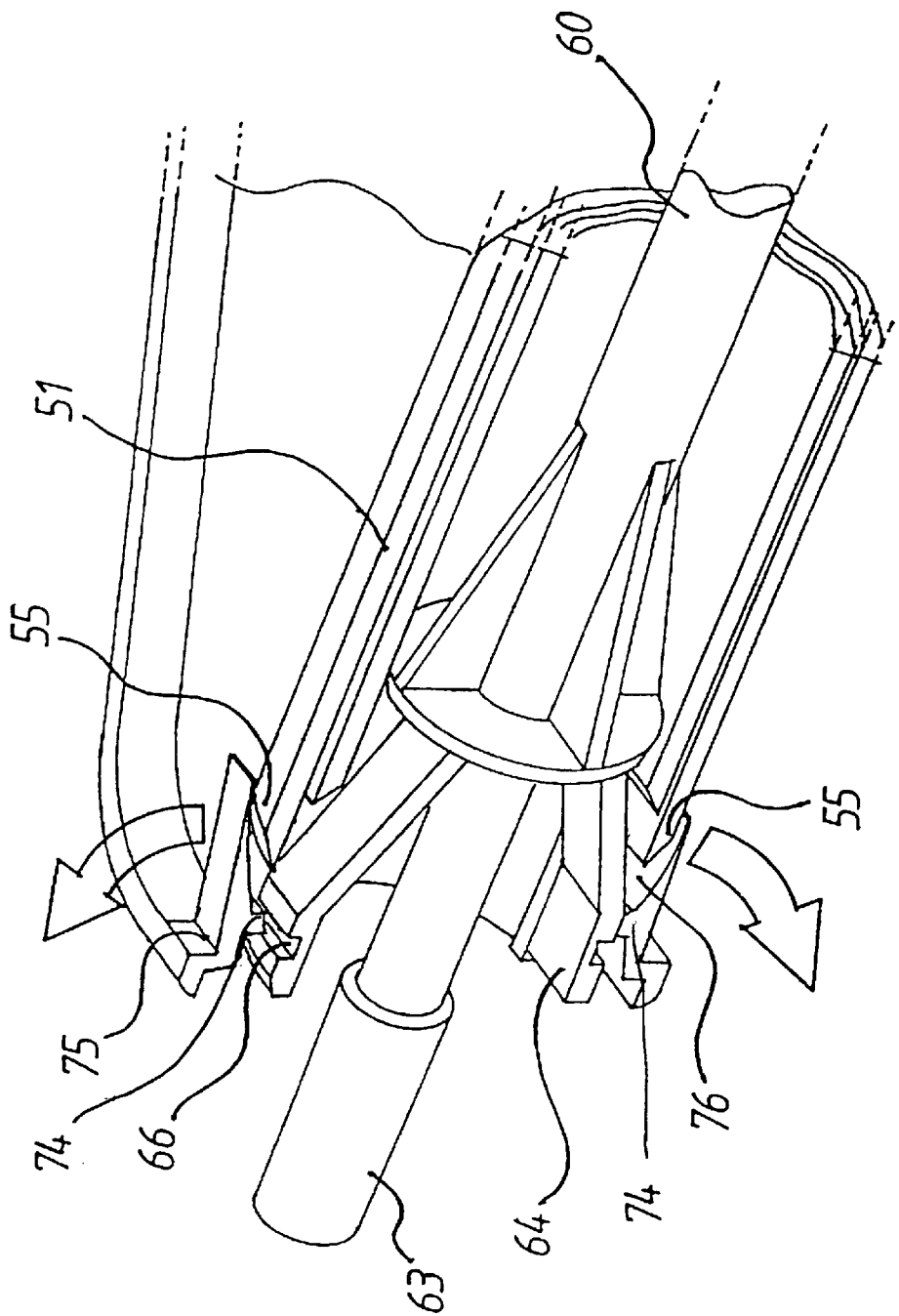
FIG. 23 is an isometric view of the configuration of FIG. 22 showing the releasing action of the flaps.

As shown in FIG. 18, the rear barbed clips (34) clip over the stops (41) of the long keyway, and the barbed clips (33) and (34) engage against the stops (41). The piston body is now locked in position in the long keyways, with the stops (41) engaged in the gap (35) between the clips. It cannot be further withdrawn, nor inserted, and any rotation is arrested by the dovetail edges (42) of the long keyway.

The barrel may be further slid right off the piston body if desired, but the needle is drawn up inside the sheath to be fully contained therein, and safe from any accidental contact.

Referring to FIGS. 19 to 23 an alternative embodiment is shown. A barrel (51) is substantially similar to the barrel of the first embodiment, of FIGS. 1 to 18, save that it has a central rod (52) extending down from a rear end (53) past a front end (54) of the barrel The front edges of the barrel (55) are chamfered downwardly towards the barrel centre.

A piston (60) (FIG. 20) has an integral piston head (61), reciprocable within the barrel, and an elongate body (62) terminating in a needle fitting (63) for receiving a conventional hypodermic needle. Diametrically opposed sets of clips (64) are provided at the front end adjacent the needle fitting (63). An axial passageway (65) passes through the piston from the head to the needle end. The passageway is shaped to receive the barrel rod when the barrel is slid over the piston from the head end.

A sheath (70) has a rear end (71) and the same configuration (72) of keyways as described with reference to the first embodiment. The sheath is tubular having finger grips (73), and differs from the first embodiment in that it has front stops (74) in the form of barbed flaps, located diametrically opposed to each other.

This embodiment functions substantially similarly to the first embodiment, save that with the integral piston head (61), the clips (64) on the piston body and stops (74) on the sheath are used to unlock the piston.

The piston body clips (64) are resiliently inwardly movable, and each has a centrally located recess (66) therein. The flaps (74) are part of the wall of the sheath, and are hinged at a front end (75) with a protruding ramp catch (76) The slope of the ramp faces rearwardly, so that with the piston in the barrel, the clip (64) can move down the sheath in an arming motion and engage the flap (74) in the recess (66).

The barrel can now be withdrawn leaving the piston behind, secured by the flaps (74). This enables fluid to be drawn into the barrel through the needle. The flaps (74) are released from under the barrel, and under the biasing of the clips (64), the flaps (74) protrude slightly outwardly above the sheath surface. The fluid is discharged by depressing the barrel over the piston. On this discharge stroke the chamfered front end of the barrel contacts the protruding sheath flaps (74) and lifts them outwardly out of engagement with the piston clips (64). This position is shown in detail in FIG. 23.

The piston is now held within the barrel under friction force, and can be withdrawn with the barrel to a safe position within the sheath. The recesses (66) of the clips (64) engage with the transverse stops of the long keyway, locking the piston.

In use, the syringe is assembled by inserting the piston, located fully within the barrel, (60) into the sheath (70). This is done by inserting the clips (64) in the cam keyway, rotating them to align them in the long keyways, and sliding the piston fully into the sheath. The clips (64) bend inwardly to engage with the flaps (74), since the barrel rides over the clips (74) and holds them against outward hinging. This is shown in more detail with reference to FIG. 22.

What is claimed is:

1. A syringe comprising:

a tubular protective sheath carrying piston engaging formations and having a needle end and an opposite rear end;

a piston including an elongate piston body and a piston head, the piston having a longitudinal fluid pathway through the head and the body, the piston body being operatively locatable to extend within the sheath and be engaged by the piston engaging formations with the piston head outside the sheath and connected to and in fluid communication with the piston body; and a barrel being slidable in a discharge stroke in use over the outside of the operatively located piston head and along the sheath to a discharged position, to thereby release the piston engaging formations and grip the released piston, the barrel being oppositely slidable from the discharged position to withdraw the released piston substantially from the sheath to a safe locked position relative to the sheath;

wherein the barrel is shaped and dimensioned to be slidable over the outside of protective sheath and the piston body and sheath carry clips and stops to operatively lock the piston body relative to the sheath to hold a needle used with the syringe inside the sheath before and after use.

2. A syringe as defined in claim 1, wherein the piston body has front and rear ends, and front and rear clips thereon, the sheath has stops at its rear end, the piston body clips and stops are arranged to enable the piston body to be inserted into the sheath with the rear piston body clips engaging the sheath stops and locking the piston body against withdrawal from and insertion into the sheath, are further arranged to enable movement of the barrel to its discharged position to release the rear piston body clips and to enable the front piston body clips to engage the stops on movement of the piston body to the safe locked position.

3. A syringe as defined in claim 2, wherein the sheath has first and second axial keyway, the first keyway has a cross-sectional shape designed to guide a clip rotating therein in use into the second keyway, and the second keyway has abrupt edges designed to prevent rotational movement of a clip therein in use.

4. A syringe as defined in claim 3, wherein the first and second keyway are formed by respective pairs of diametrically opposed matching keyways, with the pairs located at 90 degrees to each other in cross-sectional orientation of the sheath.

5. A syringe as defined in claim 4, wherein each keyway of a pair has a transverse clip stop, the clip stop of the first keyway pair is located further into the sheath interior than the clip stop of the second keyway pair.

6. A syringe as defined in claim 5, wherein the front piston body clips of the piston body form keyway slides, and have opposed clipping formations, being a front formation which is able to slide over the stops in a forward direction only, and a rear formation which is able to slide over the stops in a withdrawal direction only.

7. A syringe as defined in claim 6, wherein the rear piston body clips of the piston body having opposed clipping formations, being a forward clipping formation slidable over stops on insertion into the sheath, and a rear formation which abuts the stops when the piston body is slide into the sheath.

8. A syringe as defined in claim 7, wherein the rear formation of the rear piston body clips is shaped to cooperate with the piston head, on movement of the piston head with the barrel at the end of a discharge stroke in use, to disengage the forward formation of the rear piston body clip from its stop in use.

9. A syringe as defined in claim 1, wherein the piston engaging formations on the sheath include barbed flaps arranged to engage slots on the piston.

10. A syringe as defined in claim 9, wherein the flaps are part of the sheath wall and project axially rearwardly from a hinged portion of the sheath at the needle end of the sheath, the sheath has free ends engageable by the end of the barrel at the end of a discharge stroke to hinge the flaps outwardly and out of engagement with the slots.

11. A syringe as defined in claim 10, wherein the slots are carried in diametrically opposed piston clips which extend axially from the piston body at a front end thereof, and are resiliently inwardly deformable.

12. A syringe as defined in claim 11, wherein the sheath has first and second axial keyway, the first keyway has a cross-sectional shape designed to guide a clip rotating therein into the second keyway, and the second keyway has abrupt edges designed to prevent rotational movement of a clip therein in use, each keyway has a transverse stop at the rear end of the sheath, in which the clips form keyway slides, arranged to enable insertion of the piston body into the first keyway means with the clip slots engaged in the first keyway means stop, and to enable rotation of the piston body in this location to guide the clips into the second keyway means, free of the second keyway means stop in an insertion direction of the piston body into the sheath, and further to enable the withdrawal of the piston body with the clips in the second keyway means to a position where the clip slots engage the stop at the second keyway means to lock the piston body against insertion and withdrawal.

13. A syringe as defined in claim 1, wherein the piston head is integral with the piston body.

14. A syringe as defined in claim 1, wherein the piston head is separate from the piston body and is connectable to the piston body to form the piston.

15. A syringe as defined in claim 1, wherein the protective sheath and piston body are operatively locatable relative to each other prior to use into a packaged condition in which the end of the elongate piston body remote from the piston head end is engaged in the piston engaging formation, the fluid pathway is formed by a hypodermic needle running lengthways through the piston body with its front end extending out of the piston body and contained within and protected by the sheath, and with its rear end contained within and protected by the piston body.

* * * * *

UNITED STATES PATENT AND TRADEMARK OFFICE
CERTIFICATE OF CORRECTION

PATENT NO.     : 6,132,401
DATED          : October 17, 2000
INVENTOR(S)    : Van Der Meyden et al.

It is certified that error appears in the above-identified patent and that said Letters Patent is hereby corrected as shown below:

Column 7,
Line 25, "outside of protective sheath" should be changed to -- outside of the protective sheath --

Signed and Sealed this

Sixteenth Day of September, 2003

JAMES E. ROGAN
*Director of the United States Patent and Trademark Office*